United States Patent
Kakimoto

(10) Patent No.: US 6,870,076 B1
(45) Date of Patent: Mar. 22, 2005

(54) HOMEOBOX GENES ENCODING PROTEINS PARTICIPATING IN DIFFERENTIATION

(75) Inventor: Tatsuo Kakimoto, Toyonaka (JP)

(73) Assignee: Suntory Limited, Osaka (JP)

(*) Notice: Subject to any disclaimer, the term of this patent is extended or adjusted under 35 U.S.C. 154(b) by 55 days.

(21) Appl. No.: 09/787,737

(22) PCT Filed: Jul. 21, 2000

(86) PCT No.: PCT/JP00/04904

§ 371 (c)(1),
(2), (4) Date: Mar. 22, 2001

(87) PCT Pub. No.: WO01/07618

PCT Pub. Date: Feb. 1, 2001

(30) Foreign Application Priority Data

Jul. 22, 1999 (JP) .......................................... 11-207995

(51) Int. Cl.[7] ........................ C12N 12/29; C12N 15/82; C12N 5/04; A01H 5/00
(52) U.S. Cl. ...................... 800/290; 800/278; 800/298; 536/23.1; 536/23.6; 435/468; 435/419; 435/320.1; 435/69.1
(58) Field of Search ................................ 800/290, 278, 800/298, 295; 536/23.1, 23.6; 435/468, 419, 320.1, 69.1

(56) References Cited

FOREIGN PATENT DOCUMENTS

WO    WO 99/50417    * 10/1999

OTHER PUBLICATIONS

Kotani et al (1997, DNA Research 4:291–293).*
Bowie et al (1990, Science 247:1306–10).*
McConnell et al (2001, Nature 411 (6838):709–713).*
Fourgoux–Nicol et al (1999, Plant Molecular Biology 40: 857–872).*
Kano–Murakami et al (1993, FEBS 334:365–368).*
Uberlacker et al (1994, Maize Genetics Cooperation Newsletter, No. 68, p. 24).*
Uberlacker et al (1996, The Plant Cell 8:349–362).*
S. Cho et al., "Analysis of the C–terminal region of *Arabidopsis thaliana* APETALA1 as a transcription activation domain", Plant Mol. Biol., vol. 40, No. 3, Jun. 1999, p. 419–429.
D. Wagner et al., "Transcriptional Activation of APETALA1 by Leafy", Science, vol. 285, No. 5427, Jul. 25, 1999, p. 582–584.
Klaus F. X. Mayer et al., "Role of WUSCHEL in Regulating Stem Cell Fate in the *Arabidopsis* Shoot Meristem", Cell, vol. 95, No. 6, 1998, p. 805–815.
R. D. Schneeberger et al., "Ectopic expression of the knox homeo box gene rough sheath1 alters cell fate in the maize leaf", Genes & Development, vol. 9, No. 18, 1995, p. 2292–2304.

* cited by examiner

*Primary Examiner*—Phuong T. Bui
*Assistant Examiner*—Stuart F. Baum
(74) *Attorney, Agent, or Firm*—Burns, Doane, Swecker & Mathis, L.L.P.

(57) ABSTRACT

There is provided a gene encoding a novel protein that is involved in differentiation and that has a homeodomain-like sequence. For example, there is provided a gene derived from *Arabidopsis thaliana*, said gene encoding a protein that has the amino acid sequence as set forth in SEQ ID NO: 2 or 4, that is involved in differentiation, and that has a homeodomain-like sequence. This gene can not only be used for the production of said protein and but for the control of plant regeneration, differentiation, growth, and the like by introducing said gene into a plant.

23 Claims, No Drawings

SEQUENCE LISTING

<160> NUMBER OF SEQ ID NOS: 8

<210> SEQ ID NO 1
<211> LENGTH: 1214
<212> TYPE: DNA
<213> ORGANISM: Arabidopsis thaliana
<220> FEATURE:
<221> NAME/KEY: CDS
<222> LOCATION: (36)..(1010)
<223> OTHER INFORMATION: Nucleotide sequence coding for a protein involved in differentiation

<400> SEQUENCE: 1

```
ctttagctct cgattatcat cattacacca tcatc atg tcc tcc tca aac aaa          53
                                        Met Ser Ser Ser Asn Lys
                                         1               5 aat tgg cca agc atg ttc aaa tcc aaa cct tgc aac aat aat cat cat       101
Asn Trp Pro Ser Met Phe Lys Ser Lys Pro Cys Asn Asn Asn His His
             10                  15                  20 cat caa cat gaa atc gat act cca tct tac atg cac tac tct aat tgc      149
His Gln His Glu Ile Asp Thr Pro Ser Tyr Met His Tyr Ser Asn Cys
         25                  30                  35 aac cta tca tct tcc ttt tcc tca gat cgg ata cca gat cct aaa ccg      197
Asn Leu Ser Ser Ser Phe Ser Ser Asp Arg Ile Pro Asp Pro Lys Pro
     40                  45                  50 aga tgg aat cct aaa ccg gag cag att agg ata ctc gaa tca atc ttc      245
Arg Trp Asn Pro Lys Pro Glu Gln Ile Arg Ile Leu Glu Ser Ile Phe
 55                  60                  65                  70 aat tcc ggt act att aac cca cct aga gag gag att caa aga atc cgg      293
Asn Ser Gly Thr Ile Asn Pro Pro Arg Glu Glu Ile Gln Arg Ile Arg
                 75                  80                  85
```

```
atc cgg ctt caa gaa tat ggt caa atc ggt gac gca aac gtg ttt tac    341
Ile Arg Leu Gln Glu Tyr Gly Gln Ile Gly Asp Ala Asn Val Phe Tyr
        90                  95                 100 tgg ttt caa aac cgg aaa tct cga gca aaa cac aag ctt cgt gtt cat    389
Trp Phe Gln Asn Arg Lys Ser Arg Ala Lys His Lys Leu Arg Val His
            105                 110                 115 cac aaa agc cct aaa atg tca aag aag gac aag acg gtt att cct agt    437
His Lys Ser Pro Lys Met Ser Lys Lys Asp Lys Thr Val Ile Pro Ser
    120                 125                 130 act gac gct gat cat tgt ttt ggt ttt gtt aac caa gaa acc gga tta    485
Thr Asp Ala Asp His Cys Phe Gly Phe Val Asn Gln Glu Thr Gly Leu
135                 140                 145                 150 tat ccg gtt caa aac aat gag ttg gtg gta acc gaa ccg gcc ggt ttt    533
Tyr Pro Val Gln Asn Asn Glu Leu Val Val Thr Glu Pro Ala Gly Phe
                155                 160                 165 cta ttt ccg gtt cat aat gat ccg agc gct gct caa tca gcg ttt ggt    581
Leu Phe Pro Val His Asn Asp Pro Ser Ala Ala Gln Ser Ala Phe Gly
            170                 175                 180 ttt ggc gat ttt gtt gta ccg gtg gta acg gaa gaa ggg atg gca ttc    629
Phe Gly Asp Phe Val Val Pro Val Val Thr Glu Glu Gly Met Ala Phe
        185                 190                 195 tct acc gtt aat aac ggc gtt aat ttg gag act aac gaa aat ttt gat    677
Ser Thr Val Asn Asn Gly Val Asn Leu Glu Thr Asn Glu Asn Phe Asp
200                 205                 210 aaa att ccg gcg atc aat tta tac ggc gga gat gga aat ggc ggt gga    725
Lys Ile Pro Ala Ile Asn Leu Tyr Gly Gly Asp Gly Asn Gly Gly Gly
215                 220                 225                 230 aat tgt ttt cct cct ttg act gtt cca tta acc atc aat caa tct caa    773
Asn Cys Phe Pro Pro Leu Thr Val Pro Leu Thr Ile Asn Gln Ser Gln
                235                 240                 245 gaa aaa cga gat gta gga tta tcc ggt ggt gaa gac gtc gga gat aat    821
Glu Lys Arg Asp Val Gly Leu Ser Gly Gly Glu Asp Val Gly Asp Asn
            250                 255                 260 gtt tat ccg gtg aga atg acg gtg ttt att aac gag atg cct atc gaa    869
Val Tyr Pro Val Arg Met Thr Val Phe Ile Asn Glu Met Pro Ile Glu
        265                 270                 275 gta gtg tct gga tta ttc aac gtt aag gca gct ttc gga aac gat gcc    917
Val Val Ser Gly Leu Phe Asn Val Lys Ala Ala Phe Gly Asn Asp Ala
280                 285                 290 gtt ttg atc aac tcg ttt ggc cag cct att ctt aca gat gaa ttt ggt    965
Val Leu Ile Asn Ser Phe Gly Gln Pro Ile Leu Thr Asp Glu Phe Gly
295                 300                 305                 310 gtt act tat caa cct ctc caa aat ggc gca atc tat tat ctt att        1010
Val Thr Tyr Gln Pro Leu Gln Asn Gly Ala Ile Tyr Tyr Leu Ile
                315                 320                 325 tagaagatat tgaaaagcaa atgttatggt gctatggata aatattaata taataataaa   1070
agatttctgc gatttattta gttattaatt agataagaat ttcatttctt atcttttaaa   1130
tttatgaaca atttacagga catttacatt ttcgagactt tgaaaataa agaatgaaat    1190 taagttaaaa aaaaaaaaaa aaaa                                          1214
```

<210> SEQ ID NO 2
<211> LENGTH: 325
<212> TYPE: PRT
<213> ORGANISM: Arabidopsis thaliana
<220> FEATURE:
<223> OTHER INFORMATION: Amino acid sequence coding for a protein
      involved in differentiation

<400> SEQUENCE: 2

```
Met Ser Ser Asn Lys Asn Trp Pro Ser Met Phe Lys Ser Lys Pro
1               5                   10                  15

Cys Asn Asn His His His Gln His Glu Ile Asp Thr Pro Ser Tyr
            20              25              30

Met His Tyr Ser Asn Cys Asn Leu Ser Ser Phe Ser Ser Asp Arg
            35              40              45

Ile Pro Asp Pro Lys Pro Arg Trp Asn Pro Lys Pro Glu Gln Ile Arg
50              55                  60

Ile Leu Glu Ser Ile Phe Asn Ser Gly Thr Ile Asn Pro Pro Arg Glu
65              70                  75                  80

Glu Ile Gln Arg Ile Arg Ile Arg Leu Gln Glu Tyr Gly Gln Ile Gly
                85              90                  95

Asp Ala Asn Val Phe Tyr Trp Phe Gln Asn Arg Lys Ser Arg Ala Lys
            100             105             110

His Lys Leu Arg Val His His Lys Ser Pro Lys Met Ser Lys Lys Asp
            115             120             125

Lys Thr Val Ile Pro Ser Thr Asp Ala Asp His Cys Phe Gly Phe Val
130             135             140

Asn Gln Glu Thr Gly Leu Tyr Pro Val Gln Asn Asn Glu Leu Val Val
145             150             155             160

Thr Glu Pro Ala Gly Phe Leu Phe Pro Val His Asn Asp Pro Ser Ala
            165             170             175

Ala Gln Ser Ala Phe Gly Phe Gly Asp Phe Val Val Pro Val Val Thr
            180             185             190

Glu Glu Gly Met Ala Phe Ser Thr Val Asn Asn Gly Val Asn Leu Glu
            195             200             205

Thr Asn Glu Asn Phe Asp Lys Ile Pro Ala Ile Asn Leu Tyr Gly Gly
            210             215             220

Asp Gly Asn Gly Gly Asn Cys Phe Pro Pro Leu Thr Val Pro Leu
225             230             235             240

Thr Ile Asn Gln Ser Gln Glu Lys Arg Asp Val Gly Leu Ser Gly Gly
            245             250             255

Glu Asp Val Gly Asp Asn Val Tyr Pro Val Arg Met Thr Val Phe Ile
            260             265             270

Asn Glu Met Pro Ile Glu Val Val Ser Gly Leu Phe Asn Val Lys Ala
            275             280             285

Ala Phe Gly Asn Asp Ala Val Leu Ile Asn Ser Phe Gly Gln Pro Ile
            290             295             300

Leu Thr Asp Glu Phe Gly Val Thr Tyr Gln Pro Leu Gln Asn Gly Ala
305             310             315             320

Ile Tyr Tyr Leu Ile
            325

<210> SEQ ID NO 3
<211> LENGTH: 1518
<212> TYPE: DNA
<213> ORGANISM: Arabidopsis thaliana
<220> FEATURE:
<221> NAME/KEY: CDS
<222> LOCATION: (152)..(1285)
<223> OTHER INFORMATION: Nucleotide sequence coding for a protein
      involved in differentiation

<400> SEQUENCE: 3
tttttattta tctttccttt agccattctg ttccctgtct cttcctcctc tcttttgac       60
```

```
                                                            -continued acatcacatc atcatcacat catcattcaa catcaatcat catcatatgc atacacatac   120
atctgtgttc tgcggatcga gttaattagt t atg gct tct tcg aat aga cac     172
                                   Met Ala Ser Ser Asn Arg His
                                    1               5 tgg cca agc atg ttc aag tcc aaa cct cat ccc cat caa tgg caa cat    220
Trp Pro Ser Met Phe Lys Ser Lys Pro His Pro His Gln Trp Gln His
        10                  15                  20 gac atc aac tct cct ctc ttg cct tct gct tct cac cga tct tct cct    268
Asp Ile Asn Ser Pro Leu Leu Pro Ser Ala Ser His Arg Ser Ser Pro
 25                  30                  35 ttc tct tca gga tgt gaa gtg gag agg agt cca gag cca aaa cca aga    316
Phe Ser Ser Gly Cys Glu Val Glu Arg Ser Pro Glu Pro Lys Pro Arg
 40                  45                  50                  55 tgg aat cca aag cca gag cag att cgg ata ctt gaa gca atc ttt aac    364
Trp Asn Pro Lys Pro Glu Gln Ile Arg Ile Leu Glu Ala Ile Phe Asn
                 60                  65                  70 tcc ggg atg gtg aat cct cca aga gag gag atc agg agg att agg gct    412
Ser Gly Met Val Asn Pro Pro Arg Glu Glu Ile Arg Arg Ile Arg Ala
         75                  80                  85 cag ctt caa gaa tac ggc caa gtc ggt gat gct aac gtc ttc tac tgg    460
Gln Leu Gln Glu Tyr Gly Gln Val Gly Asp Ala Asn Val Phe Tyr Trp
         90                  95                 100 ttc caa aac cgt aag tcc cgt agt aaa cac aaa ctc cgc ctc ctc cac    508
Phe Gln Asn Arg Lys Ser Arg Ser Lys His Lys Leu Arg Leu Leu His
        105                 110                 115 aac cac tcc aaa cac tct ctc cct caa acg caa ccg cag ccg cag ccg    556
Asn His Ser Lys His Ser Leu Pro Gln Thr Gln Pro Gln Pro Gln Pro
120                 125                 130                 135 caa cct tcg gct tcc tct tcc tct tcc tcc tcc tct tcc tcc tcc aaa    604
Gln Pro Ser Ala Ser Ser Ser Ser Ser Ser Ser Ser Ser Ser Ser Lys
                140                 145                 150 tcc acc aaa ccc cga aaa agc aag aac aag aac aac act aat ctc tct    652
Ser Thr Lys Pro Arg Lys Ser Lys Asn Lys Asn Asn Thr Asn Leu Ser
            155                 160                 165 ttg ggt ggt agt caa atg atg ggg atg ttt cca ccg gaa ccg gcg ttt    700
Leu Gly Gly Ser Gln Met Met Gly Met Phe Pro Pro Glu Pro Ala Phe
        170                 175                 180 ctc ttc ccg gtc tcc act gtc gga ggg ttt gaa ggt atc acc gtc tca    748
Leu Phe Pro Val Ser Thr Val Gly Gly Phe Glu Gly Ile Thr Val Ser
185                 190                 195 tcc caa tta ggg ttt ctc tcc ggt gat atg att gag caa caa aaa ccg    796
Ser Gln Leu Gly Phe Leu Ser Gly Asp Met Ile Glu Gln Gln Lys Pro
200                 205                 210                 215 gct cca acg tgt acc gga ctc ctg ctg agt gag atc atg aac ggt agt    844
Ala Pro Thr Cys Thr Gly Leu Leu Leu Ser Glu Ile Met Asn Gly Ser
                220                 225                 230 gtg agt tat gga act cat cat caa caa cac ttg agt gag aaa gaa gtt    892
Val Ser Tyr Gly Thr His His Gln Gln His Leu Ser Glu Lys Glu Val
            235                 240                 245 gaa gaa atg agg atg aag atg ttg caa cag cca cag act cag att tgt    940
Glu Glu Met Arg Met Lys Met Leu Gln Gln Pro Gln Thr Gln Ile Cys
        250                 255                 260 tac gct acc act aat cat caa ata gct tct tac aac aac aac aac aac    988
Tyr Ala Thr Thr Asn His Gln Ile Ala Ser Tyr Asn Asn Asn Asn Asn
265                 270                 275 aac aat aac atc atg ctt cat att cct ccc act act tct act gcc acc   1036
Asn Asn Asn Ile Met Leu His Ile Pro Pro Thr Thr Ser Thr Ala Thr
                280                 285                 290                 295 act att act act tcg cat tct ctc gct act gtc cca tca act tcg gac   1084
```

```
Thr Ile Thr Thr Ser His Ser Leu Ala Thr Val Pro Ser Thr Ser Asp
                300                 305                 310 cag ctt caa gtt caa gcg gac gca cga ata aga gtt ttc atc aat gaa      1132
Gln Leu Gln Val Gln Ala Asp Ala Arg Ile Arg Val Phe Ile Asn Glu
            315                 320                 325 atg gag ctt gaa gtg agc tca gga ccg ttc aat gtg agg gat gca ttt      1180
Met Glu Leu Glu Val Ser Ser Gly Pro Phe Asn Val Arg Asp Ala Phe
        330                 335                 340 ggg gaa gag gtt gtt ctg att aat tcc gcg ggt cag ccc att gtc acc      1228
Gly Glu Glu Val Val Leu Ile Asn Ser Ala Gly Gln Pro Ile Val Thr
    345                 350                 355 gat gaa tat ggc gtc gct ctt cac cct ctt caa cac gga gcc tcg tac      1276
Asp Glu Tyr Gly Val Ala Leu His Pro Leu Gln His Gly Ala Ser Tyr
360                 365                 370                 375 tat ctg atc tagtcgtgtg ggagatttga gtttgaagaa gaaattaaga              1325
Tyr Leu Ile cctgtctctt tctttcacca tctactcgta cgtaggctta atgttaaga ttttataaag     1385 tattggtttc agttacctgt tgtgacggtg tttatgtatg agtttcggac aacattcaca    1445
aaactctctc gttaaattgt tgacctaata atatatgatg tgtgtttcat tattaaaaaa    1505
aaaaaaaaaa aaa                                                       1518

<210> SEQ ID NO 4
<211> LENGTH: 378
<212> TYPE: PRT
<213> ORGANISM: Arabidopsis thaliana
<220> FEATURE:
<223> OTHER INFORMATION: Amino acid sequence coding for a protein
      involved in differentiation

<400> SEQUENCE: 4

Met Ala Ser Ser Asn Arg His Trp Pro Ser Met Phe Lys Ser Lys Pro
1               5                   10                  15

His Pro His Gln Trp Gln His Asp Ile Asn Ser Pro Leu Leu Pro Ser
            20                  25                  30

Ala Ser His Arg Ser Ser Pro Phe Ser Ser Gly Cys Glu Val Glu Arg
        35                  40                  45

Ser Pro Glu Pro Lys Pro Arg Trp Asn Pro Lys Pro Glu Gln Ile Arg
    50                  55                  60

Ile Leu Glu Ala Ile Phe Asn Ser Gly Met Val Asn Pro Pro Arg Glu
65                  70                  75                  80

Glu Ile Arg Arg Ile Arg Ala Gln Leu Gln Glu Tyr Gly Gln Val Gly
            85                  90                  95

Asp Ala Asn Val Phe Tyr Trp Phe Gln Asn Arg Lys Ser Arg Ser Lys
            100                 105                 110

His Lys Leu Arg Leu Leu His Asn His Ser Lys His Ser Leu Pro Gln
        115                 120                 125

Thr Gln Pro Gln Pro Gln Pro Gln Pro Ser Ala Ser Ser Ser Ser Ser
    130                 135                 140

Ser Ser Ser Ser Ser Lys Ser Thr Lys Pro Arg Lys Ser Lys Asn
145                 150                 155                 160

Lys Asn Asn Thr Asn Leu Ser Leu Gly Gly Ser Gln Met Met Gly Met
                165                 170                 175

Phe Pro Pro Glu Pro Ala Phe Leu Phe Pro Val Ser Thr Val Gly Gly
            180                 185                 190

Phe Glu Gly Ile Thr Val Ser Ser Gln Leu Gly Phe Leu Ser Gly Asp
        195                 200                 205
```

-continued

```
Met Ile Glu Gln Gln Lys Pro Ala Pro Thr Cys Thr Gly Leu Leu Leu
    210                 215                 220
Ser Glu Ile Met Asn Gly Ser Val Ser Tyr Gly Thr His His Gln Gln
225                 230                 235                 240
His Leu Ser Glu Lys Glu Val Glu Glu Met Arg Met Lys Met Leu Gln
                245                 250                 255
Gln Pro Gln Thr Gln Ile Cys Tyr Ala Thr Thr Asn His Gln Ile Ala
            260                 265                 270
Ser Tyr Asn Asn Asn Asn Asn Asn Asn Ile Met Leu His Ile Pro
            275                 280                 285
Pro Thr Thr Ser Thr Ala Thr Thr Ile Thr Thr Ser His Ser Leu Ala
    290                 295                 300
Thr Val Pro Ser Thr Ser Asp Gln Leu Gln Val Gln Ala Asp Ala Arg
305                 310                 315                 320
Ile Arg Val Phe Ile Asn Glu Met Glu Leu Glu Val Ser Ser Gly Pro
                325                 330                 335
Phe Asn Val Arg Asp Ala Phe Gly Glu Val Val Leu Ile Asn Ser
            340                 345                 350
Ala Gly Gln Pro Ile Val Thr Asp Glu Tyr Gly Val Ala Leu His Pro
            355                 360                 365
Leu Gln His Gly Ala Ser Tyr Tyr Leu Ile
    370                 375
```

<210> SEQ ID NO 5
<211> LENGTH: 27
<212> TYPE: DNA
<213> ORGANISM: Artificial Sequence
<220> FEATURE:
<223> OTHER INFORMATION: Primer.

<400> SEQUENCE: 5
gaagatctca tcatgtcctc ctcaaac                                    27

<210> SEQ ID NO 6
<211> LENGTH: 30
<212> TYPE: DNA
<213> ORGANISM: Artificial Sequence
<220> FEATURE:
<223> OTHER INFORMATION: Primer.

<400> SEQUENCE: 6
cggagctcta aataagataa tagattgcgc                                 30

<210> SEQ ID NO 7
<211> LENGTH: 32
<212> TYPE: DNA
<213> ORGANISM: Artificial Sequence
<220> FEATURE:
<223> OTHER INFORMATION: Primer.

<400> SEQUENCE: 7
gctctagaac aatggcttct tcgaatagac ac                              32

<210> SEQ ID NO 8
<211> LENGTH: 32
<212> TYPE: DNA
<213> ORGANISM: Artificial Sequence
<220> FEATURE:
<223> OTHER INFORMATION: Primer.

<400> SEQUENCE: 8
tcccccgggc tgatcagata gtacgaggct cc                              32

HOMEOBOX GENES ENCODING PROTEINS PARTICIPATING IN DIFFERENTIATION

TECHNICAL FIELD

The present invention relates to gene encoding a protein that is involved in differentiation and that has a homeodomain-like sequence. More specifically, the present invention relates to genes encoding a protein that has an ability of inducing adventitious shoots and branching and that has a homeodomain-like sequence, and uses thereof.

BACKGROUND ART

Plants generally have totipotency and, for example, can regenerate individual plants through the regeneration of adventitious shoots or adventitious embryos from undifferentiated tissues derived from somatic cells. This ability is used for, for example, the production of young-plants by cultured shoot. In addition, the technique of regenerating transformed plants via the regeneration of adventitious shoots or adventitious embryos after the introduction of genes into plant somatic cell tissues or cultured plant cells has become an indispensable technology in the field of plant biotechnology in recent years. It is generally thought that the regeneration of adventitious roots or adventitious shoots from callus, which is an undifferentiated cells or plant tissues originated from leaves, stems, and the like is regulated by the interaction of plant hormones such as auxins and cytokinins.

For plant morphogenesis, it has also been reported that a series of genes including homeobox are involved in addition to plant hormones. Homeobox genes was found as a well-conserved 183 bp DNA sequence occurring in common in certain genes that regulate the development of *Drosophila*. The 61 amino acid sequence translated from this region is called homeodomain, which takes a helix-turn-helix structure comprising three α helixes and which recognizes a specific nucleotide sequence thereby to bind DNA.

Animal homeobox genes have been elucidated to be transcription factors that control development processes, whereas for plants the KNOTTED1 (KN1) gene isolated from corn in 1991 is the first homeobox gene in higher plants (Vollbrecht et al., Nature 350: 241–243, 1991). Although veins of corn leaves are parallel ones, Knotted1 mutation results in disturbances in veins and drives formation of knot-like processes along veins, after which it was named Knotted.

On the other hand, using synthetic DNA corresponding to specifically highly conserved amino acid sequences in the homeobox that had been found in many animals, genomic DNA of a dicotyledon *Arabidopsis thaliana* was searched with a result that several homeobox genes were reported (Ruberti et al., EMBO J. 10: 1787–1791, 1991).

Homeobox genes of higher plants reported so far have been roughly grouped into five types based on the similarity of amino acid composition in the homeodomain and the structure of regions other than the homeobox domain (Tasaka, Tanpakushitu Kakusan Koso (Proteins, Nucleic Acids, Enzymes) 40(8): 1033–1042, 1995). The first type is represented by the KN1 gene of corn, the second type has the homeobox approximately in the center of a protein, of which a C-terminal end is flanked by a regularly repeated structure of leucine moieties (leucine zipper) that are involved in dimer formation of the protein. The third type has the homeodomain near the C-terminal end of a protein, and a finger structure of the metal-bound type at the N-terminal end. The fourth type, in addition to having a structure common to the third type, has repeated structures of several amino acid sequences. The fifth type has the homeobox in the N-terminal end of a protein and no other well-known characteristic structures have been found therein.

The overall homology of amino acid sequences between the different types is 32 to 58% in the homeodomain. However, as can be estimated from a report that the third helix in the homeodomain enters into the main groove of the target double stranded DNA to control transcription when a protein containing an animal homeodomain binds to DNA, this third helix has the highest homology irrespective of the type even in the gene products of plant homeoboxes. The region is thought to be essential for a homeodomain protein to bind to DNA as a transcription factor. Recently, a homeobox gene WUSCHEL was reported that does not belong to any of these five groups (Cell, 95: 805–815, 1998). Although the mutants defective in the function of the WUSCHEL gene cannot drive normal growth of apical meristem of the stem, there are no experimental reports on overexpression of the WUSCHEL gene, and it is unknown what changes may occur when the WUSCHEL gene expression is artificially enhanced.

The homeobox genes of plants have been suggested to be possibly involved in the control of organogenesis or development processes, infection protection, and regulation of material transport in the plants, details of which are not known, however. Protein having a homeobox is generally thought to serve as transcription factor, but even the target gene whose transcription is regulated by each homeodomain protein has not been elucidated. Furthermore, although the overexpression of the KN1 type among the homeobox genes causes extremely abnormal morphology, it is not known whether adventitious shoots are formed on the callus.

From the standpoint of agricultural application, a gene having a high ability of inducing adventitious shoots and branching on a cultured tissue such as callus in the tissue culture system would be considered to be useful, but there are no such genes.

DISCLOSURE OF THE INVENTION

Thus, it is an object of the present invention to provide a gene encoding a protein that is involved in differentiation and that has a homeodomain-like sequence, specifically a protein that has an ability of inducing adventitious shoots and branching, a protein encoded thereby, and uses thereof.

The inventors of the present invention conducted activation tagging using *Arabidopsis thaliana* and have obtained a gene encoding a protein that has an ability of inducing adventitious shoots and branching. The activation tagging as used herein means a method of inserting enhancer sequences at random into a plant genome to isolate mutants in which the transcription of genes downstream of the inserted enhancer has been activated.

Thus, the present invention provides a gene encoding a protein that is involved in differentiation and that has a homeodomain-like sequence. More specifically, the present invention provides a gene encoding a protein that has an ability of inducing adventitious shoots and branching, and that has a homeodomain-like sequence.

More specifically, the present invention provides a gene encoding a protein that has the amino acid sequence as set forth in SEQ ID NO: 2, that is involved in differentiation, and that has a homeodomain-like sequence. The present invention further provides a gene encoding a protein that has an amino acid sequence modified by the addition or deletion of one or a plurality of amino acids and/or replacement with other amino acids in the amino acid sequence as set forth in SEQ ID NO: 2, that is involved in differentiation, and that has a homeodomain-like sequence. The present invention further provides a gene that hybridizes to the nucleic acid as set forth in SEQ ID NO: 1, specifically its DNA or a portion thereof, and that encodes a protein that is involved in differentiation and that has a homeodomain-like sequence.

The present invention further provides a gene encoding a protein that has the amino acid sequence as set forth in SEQ ID NO: 4, that is involved in differentiation, and that has a homeodomain-like sequence. The present invention further provides a gene encoding a protein that has an amino acid sequence modified by the addition or deletion of one or a plurality of amino acids and/or replacement with other amino acids in the amino acid sequence as set forth in SEQ ID NO: 4, that is involved in differentiation, and that has a homeodomain-like sequence. The present invention further provides a gene that hybridizes to the nucleic acid as set forth in SEQ ID NO: 3, specifically its DNA or a portion thereof, and that encodes a protein that is involved in differentiation, and that has a homeodomain-like sequence.

As used herein, a protein that is involved in differentiation and that has a homeodomain-like sequence is a protein that is involved in the process in which cells differentiate into morphologically and/or functionally different cells such as differentiation into adventitious shoots, branches, leaves, flowers or the like, and that has a homeodomain-like sequence functioning as a DNA-binding domain, and specifically a protein that induces the formation of adventitious shoots, a protein that induces branching, and the like.

The present invention also provides vectors comprising the gene.

The present invention further provides hosts transformed with the vector. The hosts may be plant cells or plants.

The present invention also provides a method for producing a protein that is involved in differentiation and that has a homeodomain-like sequence by culturing and/or cultivating the above host.

The present invention also provides a method for inducing differentiation of plants or plant cells, said method comprising introducing the above gene into plants or plant cells and driving the expression of said gene.

The present invention also provides a method for inducing the formation of adventitious shoots of plants or plant cells, said method comprising introducing the above gene into plants or plant cells and driving the expression of said gene.

The present invention also provides a method for inducing branch formation of plants said method comprising introducing the above gene into plants and driving the expression of said gene.

EMBODIMENT FOR CARRYING OUT THE INVENTION

The inventors of the present invention investigated the possibility of identifying a gene involved in differentiation that leads to the induction of adventitious shoot formation on a callus when overexpressed by activation tagging. Thus, *Arabidopsis thaliana*-transformed calluses into which an activation tagging vector pPCVICEn4HPT had been introduced via *Agrobacterium* were screened on a cytokinin-free medium to isolate a transformant that formed adventitious shoots even in the absence of cytokinin (an adventitious shoot is not usually formed in the absence of cytokinin). Among them, a transformant designated "many shoot" (msh) formed adventitious shoots in the absence of cytokinin.

When the MSH gene that caused the phenotype of the msh mutant and the corresponding MSH cDNA were isolated and analyzed, it was found that the protein encoded by the MSH gene has an amino acid sequence having a significant homology with homeodomain, and, among others, the third a helix domain of the homeodomain conserved in a series of homeodomain proteins had a high homology. In addition, when the coding region of MSH cDNA was introduced into an *Arabidopsis thaliana* callus and was overexpressed, as can be indicated from the phenotype of the msh mutant, the transformed callus formed an adventitious shoot in the presence or absence of cytokinin in the medium. It was also found that in *Arabidopsis thaliana* transformants in which MSH cDNA was overexpressed, branching was more frequent than in the wild type *Arabidopsis thaliana*, and adventitious shoots were occasionally formed on the leaves.

The foregoing revealed that the MSH gene is involved in differentiation and encodes a protein having a homeodomain-like sequence, which indicated the possibility that the overexpression of this might result in enhanced ability of forming adventitious shoots and branching.

As the gene of the present invention, there can be mentioned one that encodes the amino acid sequence as set forth in SEQ ID NO: 2 or 4. However, it is known that a protein that has an amino acid sequence modified by the addition or deletion of one or a plurality of amino acids and/or replacement with other amino acids retain similar effects to the native protein. Thus, the present invention encompasses a protein that has an amino acid sequence modified by the addition or deletion of one or a plurality of amino acids and/or replacement with other amino acids in the amino acid sequence as set forth in SEQ ID NO: 2 or 4, and a gene encoding said protein.

As used herein, the degree of modification is one that is possible by means known prior to the filing of the present application such as site-directed mutagenesis and PCR. The number of amino acids targeted for modification while maintaining the ability of inducing adventitious shoots and branching is for example 50 or less, preferably 25 or less, for example 10 or less.

The present invention also provides a gene that hybridizes to the nucleic acid as set forth in SEQ ID NO: 1 or 3, specifically its DNA or a portion thereof under a stringent condition, and that encodes a protein that is involved in differentiation and that has a homeodomain-like sequence. The stringent condition as used herein means a condition in which hybridization occurs, for example, 5×SSC and 50° C. A suitable hybridization temperature may be selected as appropriate since it varies with the nucleotide sequence or the length of the nucleotide sequence.

The above portion of a nucleic acid is a portion that encodes a sequence comprising at least several contiguous amino acids, and preferably a portion that encodes a sequence comprising at least several contiguous amino acids in the homeodomain. More preferably, it means a portion or a fragment that contains a part or all of the homeodomain sequence in the sequence as set forth in SEQ ID NO: 1 or 3, and that has a length of 25% or greater, for example 50% or greater, and more preferably 75% or greater of the entire sequence as set forth in SEQ ID NO: 1 or 3.

As a source of the gene as a target for the above hybridization, there can be used a cDNA library, a genomic DNA library, etc. prepared from plants, microorganisms etc., and as the plant, there can be mentioned *Arabidopsis thaliana*, petunia, snapdragons, rice, corn, tabacco, poplar, and the like.

The nucleotide sequence of the thus obtained gene encoding a protein that is involved in differentiation and that has a homeodomain-like sequence has a homology of 50% or greater, 60% or greater, preferably 70% or greater or 80% or greater, for example 90% or greater with the nucleotide sequence as set forth in SEQ ID NO: 1 or 3.

The gene of the present invention encoding a protein having the amino acid sequence as set forth in SEQ ID NO: 2 or 4 may be obtained from *Arabidopsis thaliana* as cDNA or genomic DNA.

As specifically shown in the examples, genes having the native nucleotide sequence can be obtained by, for example, screening cDNA libraries. DNA encoding a protein having a modified amino acid sequence can also be synthesized based on the DNA having the native nucleotide sequence by conventionally used site-directed mutagenesis or a PCR method. For example, a DNA fragment to be modified may be obtained by treating the native cDNA or genomic DNA with restriction enzymes, and using this as a template, site-directed mutagenesis or a PCR method is carried out using a primer into which the desired mutation has been introduced so as to obtain a DNA fragment into which the desired modification has been introduced. Then the mutation-introduced DNA fragment may be linked to a DNA fragment encoding another part of the protein of interest.

Alternatively, in order to obtain a DNA encoding a protein comprising a shortened amino acid sequence, a DNA encoding an amino acid sequence longer than the amino acid sequence of interest, for example a full-length amino acid sequence, is cleaved by a desired restriction enzyme, and when the resulting DNA fragment was found not to encode the entire amino acid sequence of interest, a DNA fragment comprising the lacking sequence is synthesized and ligated thereto.

By expressing the obtained gene using a gene expression system in *Escherichia coli* or yeast, the gene product MSH protein may be obtained. Alternatively, the MSH protein may be obtained by using an antibody against a protein encoded by the amino acid sequence as set forth in SEQ ID NO: 2 or 4. By using an antibody, the gene of a protein having a similar function to MSH may be cloned from another organism.

Thus, the present invention also relates to a recombinant vector comprising the above-entioned gene, specifically an expression vector, and a host transformed with said vector. As a host, there can be used a prokaryotic or eukaryotic organism. As a prokaryotic organism, there can be used such a common host as a microorganism belonging to the genus *Escherichia* such as *Escherichia coli*, a microorganism belonging to the genus *Bacillus* such as *Bacillus subtilis*, and the like.

As an eukaryotic host, there can be used a lower eukaryotic organism, for example an eukaryotic microorganism, for example a fungus, yeast or a sold. As yeast, there can be mentioned a microorganism belonging to the genus *Saccharomyces* such as *Saccharomyces cerevisiae*, and as a mold, there can be mentioned a microorganism belonging to the genus *Aspergillus* such as *Aspergillus oryzae* and *Aspergillus niger*, and a microorganism belonging to the genus *Penicillium*. Furthermore, animal cells or plant cells can be used as animal calls, there can be used cell lines derived from mouse, hamster, monkey, human and the like, specifically COS cells, Vero cells, CHO cells, L cells, C127 cells, BALB/c3T3 cells, Sp-2/0 cells, and the like. As plant cells, there can be used cultured cells from tobacco, genus *Populus*, genus *Eucalyptus*, genus *Acacia*, and the like.

Insect cells such as silkworm calls or adult silkworms per se can also be used as hosts. Specifically, insect cells such as cells of *Spodoptera frugiperda*, cells of *Bombyx mori*, etc. may be used.

As vectors, there can be used plasmid, phage, phagemid, virus (baculovirus (insect cell expression system), vaccinia virus (animal cell expression system)) and the like.

The vectors of the present invention may contain expression regulatory regions such as a promoter, a terminator, an origin of replication, and the like, depending on the host into which said vector is to be introduced. As promoters for bacterial expression vectors, there can be used commonly used promoters such as trc promoter, tac promoter, lac promoter, and the like; as promoters for yeasts, there can be used glyceraldehyde-3-phosphate dehydrogenase promoter, PH05 promoter, adhI promoter, pqk promoter and the like; and as mold promoters, there can be used amylase promoter, trpC promoter, and the like.

As promoters for insects, there can be mentioned the baculovirus polyhedrin promoter etc.; as animal cells, there can be mentioned the early and late promoter of Simian Virus 40, CVM promoter, HSV-TK promoter or SRα promoter, and the like.

Furthermore, as promoters for plants, there can be mentioned CaMV35S promoter, nopaline synthase promoter; as inducible promoters, there can be mentioned a promoter of the glutathione S-transferase II system genes, hsp80 promoter, the promoter of ribulose-2-phosphate carboxylase small subunit gene, and the like. Furthermore, preferred expression vectors may contain, in addition to the above, an enhancer, a splicing signal, polyA addition signal, a selectable marker such as dihydrofolate reductase gene (methotrexate-resistant) and neo gene (G418-resistant), and the like. When an enhancer is contained, the enhancer of SV40, for example, may be inserted into upstream or downstream of the gene.

The transformation of the host with an expression vector may be conducted according to a conventional method well known to a person skilled in the art, which is described in, for example, Current Protocols in Molecular Biology, John Wiley & Sons, 1995. The culturing of transformants can also be conducted according to a conventional method. Purification of a protein from the culture may be conducted by, for example, gel filtration, various column chromatography such as one that employs Sepharose, and the like. When it is expressed as a fusion protein with GST or polyhistidine in the host, it can be easily purified by suitable affinity chromatography.

Given the current state of the art, the promotion of differentiation such as adventitious shoot formation or branching formation in plants such as roses for which plant regeneration is difficult even by artificial control such as the use of plant hormones can be attained by ligating cDNA or genomic DNA under the control of a constitutive or an inducible promoter, introducing the gene into a plant in a system that employs *Agrobacterium*, particle gun, or electroporation, and driving the expression thereof.

Furthermore, it will be possible to change the morphology of garden plants, for example changing a standard type into a spray type, by regulating the expression of the gene of the present invention and, as a result, to increase the number of flowers and leaves.

EXAMPLES

The present invention will now be explained in further details with reference to the following Examples. Molecular

Example 1
Screening of a Cytokinin Responsive Mutant

In order to obtain a mutant that exhibits cytokinin response even in the absence of cytokinin by increasing the amount of the transcribed gene involved in differentiation such as adventitious shoot formation and branching formation, activation tagging was conducted using *Arabidopsis thaliana*.

About 50,000 calluses of *Arabidopsis thaliana* were transformed with a vector pPCVICEn4HPT (Hayashi et al., Science, 258: 1350–1353, 1992) for activation tagging according to the method of Akama et al. (Akama et al., Plant Cell Rep., 12: 7, 1992). Since pPCVICEn4HPT has a strong enhancer sequence derived from the CaMV35S promoter, the transcription of gene adjacent to the enhancer sequence is activated after its insertion into the plant genome. After transformation, the transformed calluses were cultured in a cytokinin-free medium.

Although the cellular growth of the wild type (non-transformed) *Arabidopsis thaliana* callus is suppressed and adventitious shoots cannot be formed in the cytokinin-free medium, some of the transformed calluses formed adventitious shoots even in the absence of cytokinin. Of them, a transformant that has a high ability of forming adventitious shoots and that forms many adventitious shoots was designated the msh (many shoot) transformant. When seeds obtained from the msh mutant were sown on a conventional agar medium for culturing *Arabidopsis thaliana*, many adventitious shoots were observed on the cotyledons.

Example 2
Isolation of the Causative Gene MSH of the msh Mutant

Genomic DNA was extracted from the msh mutant obtained in Example 1. After this genomic DNA was treated with a restriction enzyme SacI, DNA was purified, and the DNA fragment was circularized with T4 ligase. This was introduced into *Escherichia coli* and then plasmid was collected from *Escherichia coli* that acquired ampicillin resistance. The plasmid thus collected contains genomic sequences adjacent to the right border (RB) of T-DNA and most regions of T-DNA in the msh mutant.

The nucleotide sequence of 5610 bp genomic DNA adjacent to the RB was determined, and the obtained nucleotide sequence was analyzed by the GENSCAN algorithm, as developed by Chris Burge in the research group of Samuel Karlin, Department of Mathematics, Stanford University, to predict the presence of a gene. The GENSCAN program and the model that underlies it are described in Burge et al. "Prediction of complete gene structures in human genomic DNA," *J. Mol. Biol*, 268, 78–94 (1997). As a result, it was found that the transcription of the gene which is closest to RB is initiated from a nucleotide at position 882 from RB, and the gene was designated MSH.

Example 3
Isolation of MSH cDNA

From the whole plant of the msh mutant and the wild type *Arabidopsis thaliana*, RNA was extracted, from which mRNA was purified using oligotex dT30 (Nippon Roche). Using this as a template, a cDNA library was created using the lambda ZAPII cDNA library synthesis kit (Stratagene) according to a method recommended by Stratagene. cDNA libraries of these msh transformant and the wild type *Arabidopsis thaliana* were screened using the MSH gene obtained in Example 2 as a probe. Even screening of about 300,000 clones from the cDNA library derived from the wild type did not yield cDNA corresponding to the MSH gene, suggesting that the expression of the MSH gene in the wild type *Arabidopsis thaliana* is very weak or it is expressed in specific cell alone.

On the other hand, by screening about 20,000 clones of the cDNA library derived from the msh transformant, 31 positive clones were obtained, of which a clone designated M6 was used for the subsequent analysis. The nucleotide sequence of the M6 clone was determined, and the sequence is shown in SEQ ID NO: 1 of the sequence listing. The amino acid sequence corresponding to the nucleotide sequence is shown in SEQ ID NO: 2.

The full-length sequence of this coding region is contained in the MSH gene, and it was revealed that M6 was cDNA corresponding to the MSH gene. From the analysis of the nucleotide sequence of the cDNA, it was found that a protein encoded by the MSH gene has a significant homology with the homeodomain protein, and that the sequence corresponding to the third a helix in the homeodomain conserved between homeodomain proteins is most conserved in the protein encoded by the MSH gene. Furthermore, the amino acid sequence of the protein encoded by the MSH gene had the highest homology with the sequence of WUSCHEL among the homeodomain proteins.

However, even when compared to WUSCHEL having the highest homology with MSH among those reported proteins, the ratio of identical amino acids in the homeodomain is 42% and about 20% in the overall protein, so that it cannot be concluded whether it has a similar function to WUSCHEL based on the sequence. Of the homeodomain proteins, next to WUSCHEL the proteins of the KN1 type had the second highest homology with MSH protein. When the proteins were compared to MSH within the homeodomain for the homology, the ratio of identical amino acids was 20% or less. During the course of cloning, a cDNA clone of a sequence that had an identity of 86% within the homeodomain and 40% in the entire region with MSH cDNA was isolated and was designated M8. The nucleotide sequence is shown in SEQ ID NO: 3 of the sequence listing, and the corresponding amino acid sequence is shown in SEQ ID NO: 4.

Example 4
Formation of Adventitious Shoots by Overexpression of MSH cDNA

As was predicted in Example 2, it was analyzed whether the overexpression of the MSH gene causes the formation of adventitious shoots. From a binary vector pBE2113GUS (Plant Cell Physiology, 37: 49–59, 1996, obtained from NIAR) the GUS gene was removed by treating with restriction enzymes BamHI/SacI. Instead, a coding region of MSHM6 cDNA was amplified by PCR using primer #170 (5'-GAAGATCTCATCATGTCCTCCTCAAAC-3') (SEQ ID NO: 5) and primer #172 (51-CGGAGCTCTAAATAA-GATAATAGATTGCGC-3') (SEQ ID NO: 6), and then a DNA fragment treated with restriction enzymes BglII/SacI was integrated. By this procedure, the MSH cDNA inserted into the binary vector is placed under the control of an artificial promoter derived from CaMV35S promoter. The plasmid was designated pBE2113MSH.

pBE2113GUS and pBE2113MSH were introduced into the wild type *Arabidopsis thaliana* callus via *Agrobacterium*. Transformed cells were selected using kanamycin-resistance as an index. The transformed callus into which pBE2113GUS had been introduced required cytokinin at the time of adventitious shoot formation, whereas the callus transformed with pBE2113MSH was capable of regenerating adventitious shoots regardless of the presence of cytokinin. In the presence of cytokinin, calluses transformed with either plasmid regenerated adventitious shoots, whereas the callus transformed with pBE2113MSH regenerated adventitious shoots more rapidly than the callus transformed with pBE2113GUS. Furthermore, *Arabidopsis thaliana* callus that overexpresses CXI1 cDNA, a previously reported sensor histidine of the two-component system can form adventitious shoots in the absence of cytokinin, but the number of adventitious shoots formed was greater in the callus that is overexpressing MSH cDNA.

On the other hand, pBE2113MSH was introduced into germ cells of *Arabidopsis thaliana* using the Agrobacterium-mediated vacuum infiltration method (Bechtold et al., C.R. Acad. Sci. Paris, Life Sciences, 316: 1194–1199, 1993; Takashi Araki, Shokubutu Saibo Kogaku Series 4 (Plant Cell Engineering Series 4), Experimental Protocol for Model Plants, pp. 109–113, 1996), and young plants into which the gene was introduced were selected using kanamycin resistance as an index. The transformant *Arabidopsis thaliana* thus obtained was found to have more branching than the wild type strain.

Furthermore, concerning the function of the protein encoded by M8 cDNA that encodes a protein homologous to MSH cDNA obtained in Example 3, a fusion protein of the protein encoded by M8 cDNA and GUS was analyzed by allowing its overexpression in *Arabidopsis thaliana* plant. The coding region of M8 cDNA was amplified by PCR using primer #224 (5'-GCTCTAGAACAATGGCTTCTT-CGAATAGACAC-3') (SEQ ID NO: 7) and primer #225 (5'-TCCCCCGGGCTGATCAGATAGTACGAGGCTCC-3') (SEQ ID NO: 8), and then treated with restriction enzymes XbaI/SmaI, and the resulting gene fragment was inserted in between the XbaI/SmaI recognition sites of pBE2113GUS.

The binary vector pBE2113M8GUS thus obtained was introduced into germ cells of *Arabidopsis thaliana* using the Agrobacterium-mediated vacuum infiltration method, and young plants into which the gene had been introduced were selected using kanamycin resistance as an index. The *Arabidopsis thaliana* transformant thus obtained was found to have more branching as does the above *Arabidopsis thaliana* mutant that overexpressed the above MSHM6 cDNA.

INDUSTRIAL APPLICABILITY

The above data suggested that the gene MSH obtained by activation tagging from *Arabidopsis thaliana* is a homeobox gene involved in adventitious shoot formation, and is estimated to encode a transcription factor of the gene involved in adventitious shoot formation. Based on the results of overexpression of MSH cDNA under the control of the 35S promoter, it was suggested that MSH promotes adventitious shoot formation regardless of the presence of cytokinin, and, besides, that it is also involved in branching of plants.

From the foregoing, it is now possible to control adventitious shoot formation and branching formation from plants or plant cells by regulating the expression of the MSH gene.

What is claimed is:

1. An isolated polynucleotide encoding a protein that has the amino acid sequence as set forth in SEQ ID NO 2.

2. An isolated polynucleotide that encodes a protein that has at least 90% amino acid identity to SEQ ID NO: 2, wherein overexpression of said polynucleotide in a plant induces adventitious shoots and branching.

3. The polynucleotide according to claim 1 wherein said protein induces adventitious shoots when expressed in a plant.

4. The polynucleotide according to claim 1 wherein said protein induces branching when expressed in a plant.

5. A vector comprising the polynucleotide according to claim 1.

6. A host transformed with the vector according to claim 5.

7. A method for producing a protein that in regulates differentiation in a plant, wherein said differentiation is selected from the group consisting of formation of adventitious shoot and branching, said method comprising culturing or growing the host according to claim 6 and then harvesting said protein from said host.

8. The method for producing a protein according to claim 7, wherein said protein induces adventitious shoots when expressed in a plant.

9. The method for producing a protein according to claim 7, wherein said protein has an ability of inducing branching when expressed in a plant.

10. A plant or a plant cell into which the polynucleotide according to claim 1 has been introduced.

11. A method for inducing differentiation in a plant or a plant cell, wherein said differentiation is selected from the group consisting of formation of adventitious shoot and branching, said method comprising introducing the polynucleotide according to claim 1 into a plant or a plant cell and then expressing said polynucleotide, wherein the expression of said polynucleotide induces differentiation in a plant or plant cell.

12. A method for inducing adventitious shoot formation in a plant, said method comprising introducing the polynucleotide according to claim 1 into a plant and then expressing said polynucleotide, wherein the expression of said polynucleotide induces adventitious shoot formation in a plant.

13. A method for inducing branching of a plant, said method comprising introducing the polynucleotide according to claim 1 into a plant and then expressing said polynucleotide, wherein the expression of said polynucleotide induces branching in a plant.

14. The polynucleotide according to claim 2, wherein said protein induces adventitious shoots when expressed in a plant.

15. The polynucleotide according to claim 2, wherein said protein induces branching when expressed in a plant.

16. A vector comprising the polynucleotide according to claim 2.

17. A host transformed with the vector according to claim 16.

18. A plant or a plant cell into which the polynucleotide according to claim 2 has been introduced.

19. A method for inducing differentiation in a plant or a plant cell, wherein said differentiation is selected from the group consisting of formation of adventitious shoot and branching, said method comprising introducing the polynucleotide according to claim 2 into a plant or a plant cell and then expressing said polynucleotide, wherein the expression of said polynucleotide induces differentiation in a plant or plant cell.

20. A method for inducing adventitious shoot formation in a plant, said method comprising introducing the polynucleotide according to claim 2 into a plant and then expressing said polynucleotide, wherein the expression of said polynucleotide induces adventitious shoot formation in a plant.

21. A method for inducing branching of a plant, said method comprising introducing the polynucleotide according to claim 2 into a plant and then expressing said polynucleotide, wherein the expression of said polynucleotide induces branching in a plant.

22. The polynucleotide of claim 2, wherein the number of amino acids of SEQ ID NO: 2 that have been modified is 25 or less.

23. The polynucleotide of claim 22, wherein the number of amino acids of SEQ ID NO: 2 that have been modified is 10 or less.

* * * * *

UNITED STATES PATENT AND TRADEMARK OFFICE
CERTIFICATE OF CORRECTION

| | | |
|---|---|---|
| PATENT NO. | : 6,870,076 B1 | Page 1 of 1 |
| APPLICATION NO. | : 09/787737 | |
| DATED | : March 22, 2005 | |
| INVENTOR(S) | : Tatsuo Kakimoto | |

It is certified that error appears in the above-identified patent and that said Letters Patent is hereby corrected as shown below:

COLUMN 21:

Line 17, "in" should be deleted.

Signed and Sealed this

Thirtieth Day of January, 2007

JON W. DUDAS
*Director of the United States Patent and Trademark Office*